US009552969B2

(12) United States Patent
Giles et al.

(10) Patent No.: US 9,552,969 B2
(45) Date of Patent: Jan. 24, 2017

(54) ION MOBILITY SEPARATION DEVICE (71) Applicant: Micromass UK Limited, Wilmslow (GB)

(72) Inventors: Kevin Giles, Stockport (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 198 days.

(21) Appl. No.: 14/367,613

(22) PCT Filed: Dec. 21, 2012

(86) PCT No.: PCT/GB2012/053254
§ 371 (c)(1),
(2) Date: Jun. 20, 2014

(87) PCT Pub. No.: WO2013/093513
PCT Pub. Date: Jun. 27, 2013

(65) Prior Publication Data
US 2014/0353487 A1    Dec. 4, 2014

Related U.S. Application Data (60) Provisional application No. 61/580,547, filed on Dec. 27, 2011.

(30) Foreign Application Priority Data
Dec. 23, 2011    (GB) .................................. 1122251.1

(51) Int. Cl.
*H01J 49/00*    (2006.01)
*G01N 27/62*    (2006.01)
(Continued)

(52) U.S. Cl.
CPC ......... *H01J 49/0031* (2013.01); *G01N 27/622* (2013.01); *H01J 49/062* (2013.01);
(Continued)

(58) Field of Classification Search
USPC .......................... 250/286, 291, 292, 281, 282
See application file for complete search history.

(56) References Cited

U.S. PATENT DOCUMENTS 5,227,628 A    7/1993  Turner
7,776,043 B2   8/2010  Nycz et al.
(Continued)

OTHER PUBLICATIONS

Clemmer et al., "*High Resolution Ion Cyclotron Mobility Spectrometry*", Anal. Chem., vol. 81, pp. 1482-1487, 2009.

*Primary Examiner* — Kiet T Nguyen
(74) *Attorney, Agent, or Firm* — Diederiks & Whitelaw, PLC (57) ABSTRACT An ion mobility separator 4 and a method of separating ions according to their ion mobility are disclosed. An RF ion guide is provided having a plurality of electrodes that are arranged to form an ion guiding path that extends in a closed loop. RF voltages are supplied to at least some of the electrodes in order to confine ions within said ion guiding path. A DC voltage gradient is maintained along at least a portion of a longitudinal axis of the ion guide, wherein the voltage gradient urges ions to undergo one or more cycles around the ion guide and thus causes the ions to separate according to their ion mobility as the ions pass along the ion guide. The closed loop ion guide enables the resolution of the ion mobility separator to be increased without necessitating a large device, since the drift length through the device can be increased by causing the ions to undergo multiple cycles around the device.

30 Claims, 8 Drawing Sheets (51) Int. Cl.
*H01J 49/06* (2006.01)
*H01J 49/42* (2006.01)
*H01J 49/36* (2006.01)

(52) U.S. Cl.
CPC ............ *H01J 49/065* (2013.01); *H01J 49/36* (2013.01); *H01J 49/4235* (2013.01)

(56) References Cited

U.S. PATENT DOCUMENTS

| | | |
|---|---|---|
| 7,838,821 B2 | 11/2010 | Clemmer et al. |
| 8,067,747 B2 | 11/2011 | Wollnik |
| 8,258,467 B2 | 9/2012 | Kajihara |
| 8,362,420 B2 | 1/2013 | Clemmer et al. |
| 8,415,618 B2 | 4/2013 | Hoyes |
| 8,552,366 B2 | 10/2013 | Hoyes |
| 2009/0014641 A1 | 1/2009 | Bateman et al. |
| 2011/0266435 A1* | 11/2011 | Hoyes ................. G01N 27/622 250/282 |
| 2014/0042315 A1* | 2/2014 | Baykut ................ G01N 27/622 250/290 |

* cited by examiner

ION MOBILITY SEPARATION DEVICE

CROSS-REFERENCE TO RELATED APPLICATION

This application is the National Stage of International Application No. PCT/GB2012/053254, filed 21 Dec. 2012, which claims priority from and the benefit of U.S. Provisional Patent Application Ser. No. 61/580,547 filed 27 Dec. 2011 and United Kingdom Patent Application No. 1122251.1 filed on 23 Dec. 2011. The entire contents of this application is incorporated herein by reference.

BACKGROUND OF THE PRESENT INVENTION

It is known to apply a uniform electric field across a drift region of an ion mobility spectrometer (IMS) in order to separate ions according to their ion mobilities. It is desirable to provide such devices with relatively high resolution. It is possible to increase the resolution of such a device by increasing the electric field strength in the drift region. However, this will ultimately result in electrical breakdown in the drift gas. In order to increase the resolution of the device it is therefore conventionally considered necessary to increase the length of the drift region, whilst maintaining the electric field strength. However, this leads to a relatively long IMS device and the use of a larger potential difference in order to maintain the same electric field strength over the longer drift region. This necessitates the use of high absolute voltages, which may result in hazardous electrical discharges to the surrounding areas.

It is therefore desired to provide an improved ion mobility separator and an improved method of separating ions according to their ion mobility.

SUMMARY OF THE PRESENT INVENTION

The present invention provides a method of separating ions according to their ion mobility comprising:

providing an RF ion guide having a plurality of electrodes arranged to form an ion guiding path that extends in a closed loop;

supplying RF voltages to at least some of said electrodes in order to confine ions within said ion guiding path; and maintaining a DC voltage gradient along at least a portion of a longitudinal axis of said ion guide, wherein said voltage gradient urges ions to undergo one or more cycles around said ion guide and thus causes the ions to separate according to their ion mobility as they pass along the ion guide.

Conventionally it has been necessary to employ a relatively long drift region in order to obtain the desired resolution of ion mobility separation. The closed loop ion guide of the present invention enables the resolution of the ion mobility separation to be increased without necessitating a large device, since the drift length through the device can be increased by causing the ions to undergo multiple cycles around the device.

The ion guide preferably comprises an ion entry/exit region configured for introducing ions into the ion guide in one mode and for extracting ions from the ion guide in another mode, wherein the ion entry/exit region is at a fixed location on the ion guide.

Preferably, the electrodes of the ion guide are axially spaced along the longitudinal axis of the ion guide and different DC voltages are applied to different ones of said axially spaced electrodes so as to form said DC voltage gradient.

The DC voltage gradient region described herein is preferably defined over a length of the ion guide extending from a first electrode at a relatively high potential to a second electrode at a relatively low potential. Progressively smaller DC potentials are preferably applied to electrodes between the first and second electrodes in a direction from the first electrode to the second electrode so as to form said voltage gradient. This differs from arrangements wherein a voltage step or barrier is conveyed along a series of electrodes. It is also preferred in the present invention that the ions separate out according to their ion mobility within the DC voltage gradient region.

It is preferred that a substantially uniform DC voltage gradient is arranged along the DC voltage gradient region. In embodiments wherein the ion guide is formed from axially spaced electrodes, this may be achieved by providing relatively small potential differences between pairs of adjacent electrodes in the DC voltage gradient region such that the DC potential decreases progressively and gradually along this region.

Preferably, as time progresses the portion of the ion guide along which the DC voltage gradient is maintained is moved along the ion guide. For example, the DC voltage gradient may chase the ions along the ion guide such that the ions remain within the DC voltage gradient, even as they pass around the ion guide. This may be advantageous in that a relatively small potential difference can be used to set up a relatively large electric field strength over a relatively small region, and this region can then be moved along the ion guide such that the ions remain in the relatively high strength electric field as they travel around the ion guide. The ions can therefore be separated in an electric field region of relatively high strength but without having to apply such a high electric field strength along the whole ion guide at any given time, which would require a larger potential difference to be applied across a longer length.

Alternatively, or additionally, the voltage gradient may be moved such that the ions can remain on the same DC voltage gradient as they pass around the ion guide multiple times. If the DC voltage gradient remained in a fixed location and the ions passed around the ion guide multiple times then at some point the ions would have to make a transition from the low potential end of the voltage gradient back to the high potential end of the voltage gradient. It is undesirable that the ions travel across such a voltage discontinuity since it is desired that the ions only travel through a substantially uniform and continuous DC voltage gradient during their ion mobility separation.

The DC voltage gradient preferably moves around the ion guide at a rate such that at least some of said ions continually remain within the DC voltage gradient region as they travel around the ion guide and preferably until such ions are extracted from the ion guide at an exit region of the ion guide. The ions may remain within the DC voltage gradient as they travel only a single cycle around the closed loop ion guide. Alternatively, the ions may remain within the DC voltage gradient as they repeatedly travel multiple cycles around the closed loop ion guide.

The DC voltage gradient may be moved around the ion guide at a rate such that undesired ions having an ion mobility above a first threshold value and/or below a second threshold value do not continuously remain within the voltage gradient region as the region is moved around the ion guide. The rate at which the voltage gradient is moved around the ion guide may cause undesired ions having an ion mobility above the first threshold value to exit the low potential end of the voltage gradient region and/or may cause undesired ions having an ion mobility below the second threshold value to exit the high potential end of the voltage gradient. The undesired ions that do not continuously remain within the DC voltage gradient region may not be extracted from the ion guide at an exit region of the ion guide.

RF voltages are applied to the electrodes so as to confine ions within the ion guiding path along the DC voltage gradient region. Such RF voltages may not be applied to at least some of the electrodes at one or more regions of the ion guide outside of the DC voltage gradient region such that ions are not confined within said one or more regions of the ion guide and are lost from the ion guide at these regions. This is an efficient method of removing undesired ions that do not remain on the DC voltage gradient.

The rate at which the DC voltage gradient moves around the ion guide may be synchronised with the rate at which ions of interest are urged around the ion guide by the voltage gradient such that the ions of interest reach an exit region of the ion guide at a time when the minimum potential of the voltage gradient is arranged at the exit region of the ion guide. This is advantageous as it may be desirable to maintain a relatively high potential region of the voltage gradient at the exit region at one time during the ion mobility separation process, but for the potential at the exit region to be low or zero at the time that the ions exit from the exit region. For example, if the exit region and entrance region are collocated at the same region, then it may be desirable that substantially the maximum potential of the voltage gradient is arranged at the entrance region at a time when the ions are in the entrance region so as to urge the ions away from the entrance region and around the ion guide, but that by the time the ions have passed around the ions guide and reached the exit region the minimum potential of the voltage gradient is arranged at the exit region, e.g. to enable efficient extraction of the ions from the exit region.

The DC voltages are preferably only applied to some of the electrodes of the ion guide such that the DC voltage gradient is arranged along only a portion of the length of the ion guide at any given time. At any given time the DC voltage gradient may be arranged over only a percentage of the length of the ion guide selected from: <5%; <10%; <20%; <30%; <40%; <50%; <60%; <70%; <80%; or <90%. Additionally, or alternatively, at any given time the DC voltage gradient may be arranged over only a percentage of the length of the ion guide selected from: >5%; >10%; >20%; >30%; >40%; >50%; >60%; >70%; >80%; or >90%. Any permutation of ranges from the above two lists may be combined.

Alternatively, the DC voltage gradient may be arranged over substantially the whole length of the ion guiding region at any given time.

The electrodes are preferably configured to confine ions in directions perpendicular to the longitudinal axis of the ion guide when said RF voltages are applied.

The electrodes are preferably apertured electrodes that are aligned such that the ions are guided through the apertures of the electrodes as they travel along the ion guiding path. Preferably, the apertures in the electrodes are slotted apertures. in this embodiment, the electrodes may be arranged such that at least a portion of the ion guiding path is curved and so has a radius of curvature, wherein each slot has its minimum dimension substantially parallel with said radius and its maximum dimension substantially perpendicular to said radius.

The electrodes are preferably arranged such that the closed loop ion guiding path is substantially circular or oval. However, any other closed loop geometry may be used.

A drift gas is preferably arranged in said ion guide such that ions separate according to their mobility through the drift gas as they are urged along the ion guide.

Ions may be introduced into or ejected out of the closed loop ion guide through a side of the ion guide. Alternatively, or additionally ions may be introduced into the closed loop ion guide through the top or bottom of the ion guide; and/or ions may be ejected out of the closed loop ion guide through the top or bottom of the ion guide.

An array of electrodes may be provided to urge ions into an entry region of the ion guide; and/or an array of electrodes may be provided in an exit region of the ion guide to urge ions out of the ion guide.

The ion guide may comprise an exit region and ions may be ejected out of ion guide at the exit region as the ions travel around the ion guide by applying a voltage pulse to one or more electrodes of the ion guide, the timing of the voltage pulse being selected so as eject ions of a selected ion mobility as they pass through the exit region.

Although the electrodes forming the ion guiding path have been described hereinabove as being apertured electrodes, it is also contemplated that other geometries of electrodes may be used to guide ions around the device. For example, the ion guide may be segmented in the longitudinal direction into a plurality of segments and each segment may comprise a plurality of electrodes arranged and configured for confining and guiding the ions. Each segment preferably comprises a top electrode, a bottom electrode and a plurality of side electrodes arranged therebetween so as to define a space between the top, bottom and side electrodes through which ions are guided. RF potentials are preferably applied to the side electrodes so as to confine ions in said space in the direction between the side electrodes. DC potentials are preferably applied to the top and/or bottom electrodes so as to confine ions in said space in the direction between the top and bottom electrodes. Less preferably, RF potentials are applied to the top and/or bottom electrodes so as to confine ions in said space in the direction between these electrodes.

Each segment may comprise a plurality of layers of side electrodes arranged between the top and bottom electrodes. Each layer preferably comprises two laterally spaced apart electrodes, which define a space therebetween for guiding ions. The side electrodes are preferably stacked in columns so as to define a space between the columns of side electrodes, and between the top and bottom electrodes. The top, bottom and side electrodes are preferably substantially planar and extend around the longitudinal direction of the drift cell so as to form a segment of the drift cell. The electrodes may be formed from printed circuit boards.

Ions may be radially confined within the space between the side electrodes, top electrode and bottom electrode by applying RF potentials to the side electrodes. The same phase of an RF voltage source is preferably applied to the two side electrodes in each layer. Different phases of the RF voltage source are preferably applied to the side electrodes in adjacent layers. The side electrodes in any given layer are preferably supplied with an opposite RF voltage phase to the side electrodes in the adjacent layers. By applying RF potentials to the side electrodes, the ions are laterally confined within the space between the side electrodes. RF potentials may also be applied to the top and bottom electrodes so as to confine ions within the space in the vertical direction. However, it is preferred that only DC potentials are applied to the top and bottom electrodes so as to confine the ions in the vertical direction.

A DC voltage gradient is preferably applied to at least some of the electrodes so as to provide an axial electric field that urges ions to drift through the drift gas and around the drift cell. The DC voltage gradient may be formed by supplying different DC voltages to the electrodes of different segments of the drift cell. Different DC voltages may be supplied to the top and/or bottom electrode in different segments so as to form the voltage gradient. Additionally, or alternatively, different DC voltages may be supplied to the side electrodes of different segments so as to form the voltage gradient. For example, progressively smaller DC voltages may be applied to the electrodes of the different segments around the drift cell so as to create a voltage gradient that drives the ions along the drift length.

The present invention also provides a method of mass spectrometry comprising separating ions according to any one of the methods described above.

The present invention also provides an ion mobility separator comprising:

an RF ion guide having a plurality of electrodes arranged to form an ion guiding path that extends in a closed loop;

an RF voltage supply for supplying RF voltages to said electrodes for confining ions within said ion guiding path; and a DC voltage supply arranged and adapted to maintain a DC voltage gradient along at least a portion of a longitudinal axis of said ion guide, wherein in use said voltage gradient urges ions to undergo one or more cycles around said ion guide and thus to cause the ions to separate according to their ion mobility as they pass along the ion guide.

The ion mobility separator may be arranged and configured to perform any one of the method of separating ions that has been described above.

The present invention also provides a mass spectrometer comprising an ion mobility spectrometer as described above.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") on source; and (xxi) an Impactor ion source; and/or (b) one or more continuous or pulsed ion sources; and/or (c) one or more additional ion guides; and/or (d) one or more additional ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser, (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser (x) a Fourier Transform electrostatic or orbitrap mass analyser; (xi) a Fourier Transform mass analyser; (xii) a Time of Flight mass analyser (xiii) an orthogonal acceleration Time of Flight mass analyser, and (xiv) a linear acceleration Time of Flight mass analyser, and/or (h) one or more energy analysers or electrostatic energy analysers; and/or (i) one or more ion detectors; and/or (j) one or more mass filters selected from the group consisting of: (i) a quadrupole mass filter, (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (ill) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xi) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The preferred embodiment provides the capability to undertake ion mobility separation around a closed loop system, wherein single or multiple passes of the ions around the loop may be undertaken. As the ion guide is formed as a closed loop the ions can pass around the loop multiple times such that the closed loop ion guide provides a relatively long drift region along which the ions can separate, whilst maintaining a relatively compact geometry.

Conventional ion mobility separator mass spectrometers generally employ relatively large ion mobility separators having relatively long, linear drift regions for providing high resolution. These systems require the use of high voltages to generate the required electric field across the long drift region. Multi-pass IMS systems have been built but suffer from relatively low sensitivity. The preferred embodiment provides high sensitivity combined with high resolution in a compact geometry through the use of an RF ion guide loop system.

The preferred embodiment helps to solve the problem of the requirement for physically long drift regions to achieve higher mobility resolution and reduces the absolute voltage required to achieve the resolution, thus minimising the use of hazardous voltages and the risk of electrical breakdown.

BRIEF DESCRIPTION OF THE DRAWINGS

Various embodiments of the present invention will now be described, by way of example only, and with reference to the accompanying drawings in which:

FIG. 5A shows a portion of the embodiment of FIG. 4A and FIGS. 5B to 5D show DC voltage potential profiles along this portion at different times during the ions separation process;

DETAILED DESCRIPTION OF PREFERRED EMBODIMENTS

The resolving power R of an ion mobility spectrometer (IMS) that uses a uniform electric field is given by the expression:

$$R = \frac{t}{t_{FWHM}} = \left(\frac{LEze}{16kT\ln 2}\right)^{0.5} = \left(\frac{Vze}{16kT\ln 2}\right)^{0.5}$$

wherein t is the ion drift time through the drift region of the device; $t_{FWHM}$ is the peak width at half height of the signal; L is the length of the drift region; E the electric field strength; z is the charge on the ion being analysed; e is the unit electronic charge; V is the potential difference across the drift region of the device (E=V/L); k is Boltzmann's constant; and T is the temperature of the drift gas in the drift region.

It is apparent from the above expression that the potential difference V across the drift region of the IMS device can be increased in order to increase the resolution of the device. However, increasing the potential difference across a fixed length of drift region will ultimately result in electrical breakdown in the drift gas. In order to further increase the resolution of the device it is therefore conventionally considered necessary to increase the length of the drift region L. However, if the length of the drift region L is increased then a greater potential difference must be applied across the drift region in order to maintain the same electric field strength over the longer drift region.

Figure 1:
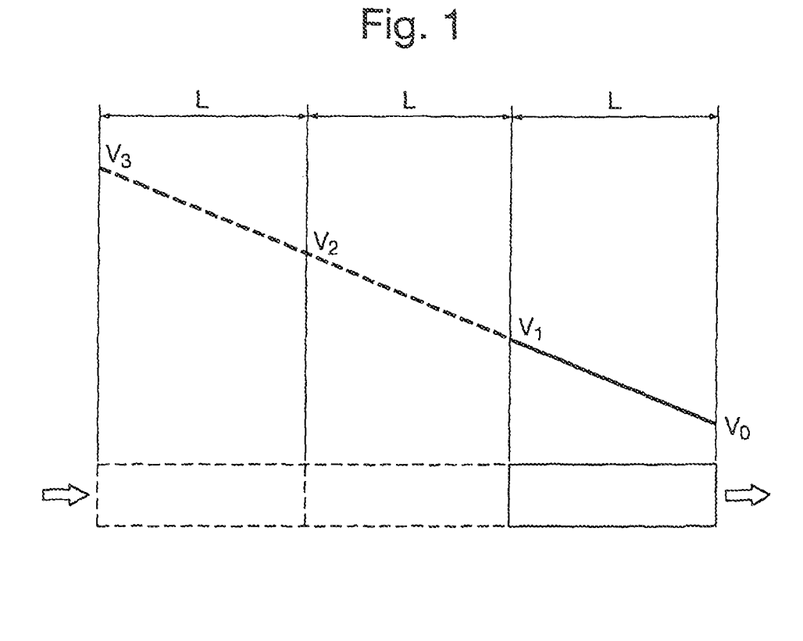
FIG. 1 shows an example of the voltages that must be applied to drift regions of different lengths in order to maintain the same electric field strength along the different lengths of drift region.

FIG. 1 shows an example of the voltages that must be applied to drift regions of different lengths in order to maintain the same electric field strength along the different lengths of drift region. If the drift region only has a length L then a voltage $V_0$ may be applied at the exit of the drift region and a higher voltage $V_1$ may be applied at the entrance to the drift region in order to provide an electric field across the drift region. The electric field drives ions through a drift gas that is present in the drift region, such that the ions separate according to their mobility through the drift gas as they pass through the drift region. If the length of the drift region is doubled to 2L and the same voltage $V_0$ is applied at the exit of the drift region, then the voltage applied at the entrance of the drift region must be increased to $V_2$ in order to maintain the same electric field strength along the drift region of length 2L as was present along the drift region of length L. Similarly, if the length of the drift region is increased to 3L and the same voltage $V_0$ is applied at the exit of the drift region, then the voltage applied at the entrance of the drift region must be increased to $V_3$ in order to maintain the same electric field strength along the drift region of length 3L as was present along the drift region of length L. This conventional approach ultimately leads to an extremely long drift region and hence a large IMS device. Also, this conventional approach requires the use of a relatively large potential difference in order to achieve the desired electric field strength along the relatively long drift region. The use of high absolute voltages to achieve this can lead to electrical breakdown to the surroundings, which can be hazardous.

In order to avoid using such high voltages and long drift regions, a desired voltage gradient may be applied over only a portion of the length of the drift region at any given time, such that the required electric field is obtained in that portion of the drift region. The voltages that provide the electric field may then be progressed along the drift region such that the portion of the drift region in which the electric field is applied keeps up with the drifting ions. This is illustrated in FIG. 2.

Figure 2:
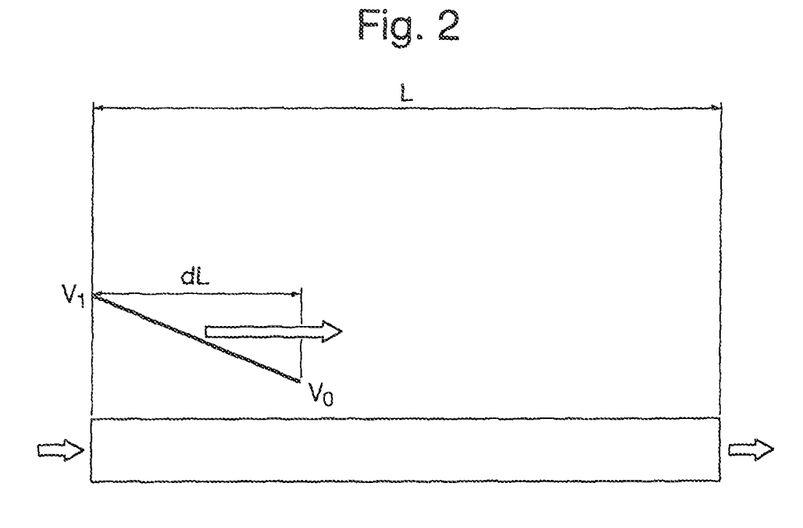
FIG. 2 shows an ion mobility separator that translates an electric field region along the drift length in order to separate ions.

FIG. 2 shows a drift region of length L. An electric field is set up along a portion of the drift region 'dL' by applying potentials $V_0$ and $V_1$ at spaced apart points of the drift region L. The electric field forces ions through the drift gas, causing them to separate according to their ions mobilities as they pass through the drift gas. As the ions progress from the entrance towards the exit of the drift region L, the portion of the drift region dL over which the electric field is applied is moved along the drift region L in a direction from the entrance to the exit of the drift region. The portion of the drift region dL over which the electric field is applied is moved at a rate such that the desired ions do not exit the electric field region dL as they pass through the drift region L. This ensures that the ions of interest experience a uniform electric field of the desired strength as they pass along the entire length of the drift region and without the need to provide a large potential difference across the whole length of the drift region L. Rather, as the electric field is only applied across a portion dL of the drift region L, a relatively small potential difference $V_1-V_0$ can be employed to achieve the desired electric field strength. This technique therefore minimises the risk of electrical breakdown that might otherwise be caused by the use of high absolute voltages.

The resolution of a device of the kind described in relation to FIG. 2 increases in proportion to the square root of the ratio L/dL, for a fixed potential difference of $V_1-V_0$ over length dL. Therefore, in order to increase the resolution of the device the total length of the drift region L must be increased or the length of the electric field region dL must be reduced. Increasing the total length of the drift region L results in an undesirably large IMS device. However, reducing the length of the electric field region dL may make it difficult to maintain the ions of interest within the electric field region dL as they pass through the drift region and spatially separate from each other.

Figure 3:
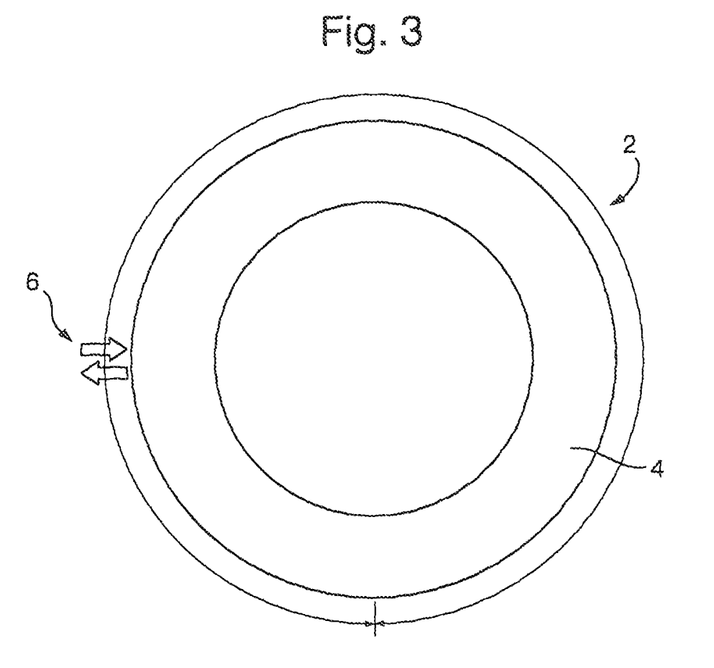
FIG. 3 shows an ion mobility separator according to an embodiment of the present invention and having a circular drift length.

FIG. 3. shows an IMS device 2 according to an embodiment of the present invention which may provide an improved resolution without suffering the above-mentioned drawbacks. The IMS device 2 comprises a drift cell 4 having electrodes for guiding ions along a drift length that is arranged as a continuous circular geometry. Ions may be introduced into the device at an entry region 6. After the ions have entered the device 2 they are caused to move around the drift length of the device by applying voltages to the electrodes of the device. More specifically, a potential difference may be arranged or conveyed along the drift length so that the ions are urged along the drift length. A drift gas is present in the drift length and causes the ions to separate out according to their ion mobilities through the drift gas as they pass along the drift length. After the ions have performed their desired separation, they may be extracted from or allowed to exit the device 2 at an exit region 6, which is preferably at the same location as the entry region 6. Ions are therefore preferably caused to perform at least one complete cycle around the drift cell 4 before being extracted, i.e. a cycle from the entry/exit region 6 of the drift cell 4 all of the way around the drift cell 4 and back to the entry/exit region 6 of the drift cell. Ions may be caused to perform only a single cycle around the drift cell 4 or to perform multiple cycles around the drift cell 4 before being extracted, depending upon the length over which the ions are desired to be separated.

As mentioned above, a potential difference may be arranged or conveyed along the drift length so as to cause the ions to cycle around the drift cell 4. If only a single cycle around the drift cell 4 is required then a fixed potential difference may be arranged across a fixed length of the drift cell 4 so as to drive the ions around the drift cell from the entrance region 6 to the exit region 6. Alternatively, a potential difference may be conveyed along the drift length so as to cause the ions to cycle around the drift cell 4. In this embodiment a potential difference for driving ions through the device 2 may be arranged over only a portion of the drift length at any given time. As the ions travel around the drift cell 4, the length of the drift region over which the potential difference is applied is conveyed around the drift cell 4 so that the desired ions are always maintained in a region across which the potential difference is applied. If the ions are only desired to travel one cycle around the drift cell 4, then the drift length across which the potential difference is applied may be caused to travel around the drift cell 4 only once. However, if the ions are desired to travel multiple cycles around the drift cell 4, then the drift length across which the potential difference is applied may be caused to travel around the drift cell 4 multiple times along with the ions. In modes wherein the ions cycle around the drift cell 4 multiple times, the ion entry and exit region 6 may be deactivated so that the ions pass the entry and exit region 6 unimpeded, until it is desired to extract the ions.

Figure 4A:
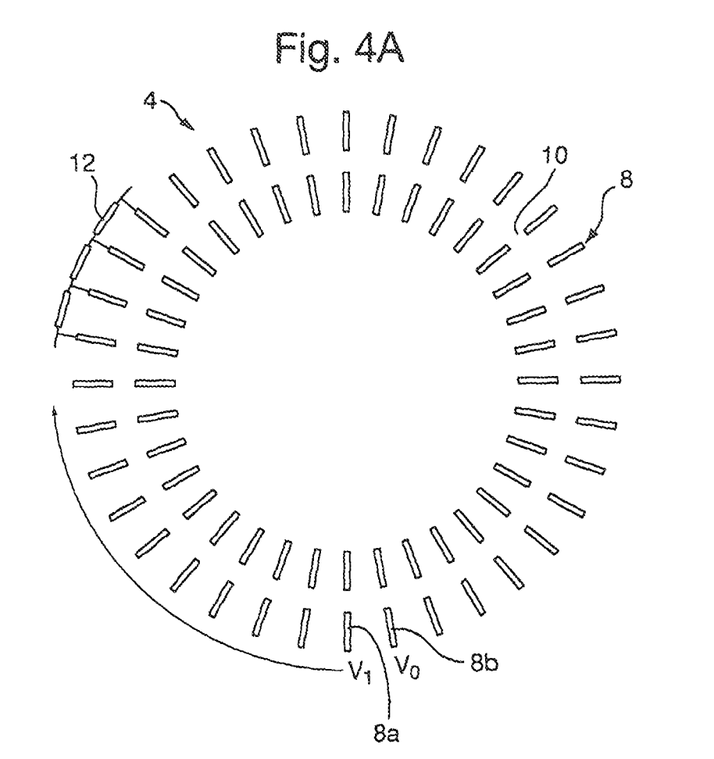
FIG. 4A shows a plan view of the arrangement of the electrodes in the embodiment of FIG. 3.
Figure 4B:
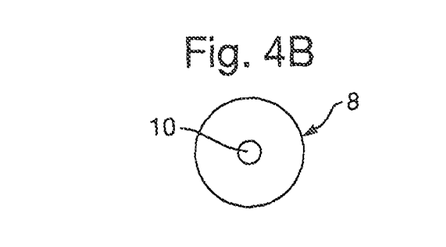
FIG. 4B shows a schematic of one of the electrodes.

FIG. 4A shows a preferred embodiment of the arrangement of the electrodes 8 in the drift cell 4 of FIG. 3 from a plan view. The drift cell 4 may be formed from a plurality of apertured electrodes 8 that are arranged in a circle and such that each electrode 8 lies in a plane that extends radially outward from the centre of the drift cell 4. An example of an apertured electrode 8 having a circular aperture 10 is shown in FIG. 4B. Voltages are applied to the electrodes 8 so as guide ions through the apertures 10 in the successive electrodes 8 and hence around the drift cell 4. More specifically, RF voltages may be applied to the electrodes 8 so as to radially confine the ions and provide an ion guiding path through the apertures 10 of the electrodes 8. Alternate electrodes 8 in the drift cell 4 are preferably applied with different phases of an RF voltage source. Alternate electrodes 8 in the drift cell 4 are preferably applied with opposite phases of the RF voltage source, i.e. when a given electrode 8 is at an RF phase of 0 degrees the adjacent electrodes 8 are preferably at 180 degrees. A DC voltage gradient is applied to at least some of the electrodes 8 and is preferably superimposed on the RF voltages so as to provide an axial electric field that urges ions to drift through the drift gas and around the drift cell 4.

In the example shown in FIG. 4A it can be seen that one electrode 8a is maintained at a relatively high voltage $V_1$ and an adjacent electrode 8b is maintained at a relatively low voltage $V_0$. This causes ions to be forced away from the electrode 8a at high voltage $V_1$ and to pass around the drift cell 4 in an anti-clockwise manner towards the electrode 8b at low voltage $V_0$. At least some of the electrodes 8 that are arranged between the two electrodes 8a,8b held at $V_1$ and $V_0$ also preferably have DC potentials applied to them so as to maintain a voltage gradient that decreases between said two electrodes 8a,8b. For example, progressively smaller DC voltages may be applied to the electrodes 8 around the drift cell 4 so as to create a voltage gradient that drives the ions along the drift length. The DC voltage gradient may be generated using a resistor chain 12 coupled to the electrodes 8 forming the drift cell 4 and across which a potential difference is applied. It will be appreciated that although a decreasing voltage gradient has been described for urging positive ions around the device, an increasing voltage gradient may be used to urge negative ions around the device.

In the above example, the DC potential difference applied to the device is arranged along a fixed length of the device. Alternatively, a DC potential difference may be arranged along only a portion of the length of the drift region so as to form an axial electric field region and this axial electric field region may then be moved around the device with the ions. In the latter embodiment, DC voltages may be applied to only some of the electrodes 8 forming the drift cell 4 so as to form a DC voltage gradient and axial electric field region along only a portion of the drift cell 4. The electrodes 8 to which these DC voltages are applied may then be changed with time so that length over which the axial electric field is maintained is moved around the drift cell, preferably in a manner such that as the ions pass around the drift cell they always remain within the electric field region. This ensures that the ions experience a uniform electric field strength as they pass around the drift cell 4. The axial DC voltage gradient may be progressively stepped around the device in steps of single electrodes 8 or in steps of multiple electrodes 8. However, it is observed that increasing the number of electrodes 8 by which the voltage gradient is stepped around the device effectively reduces the range of ion mobilities which can be retained in the axial electric field region.

Figure 5A:
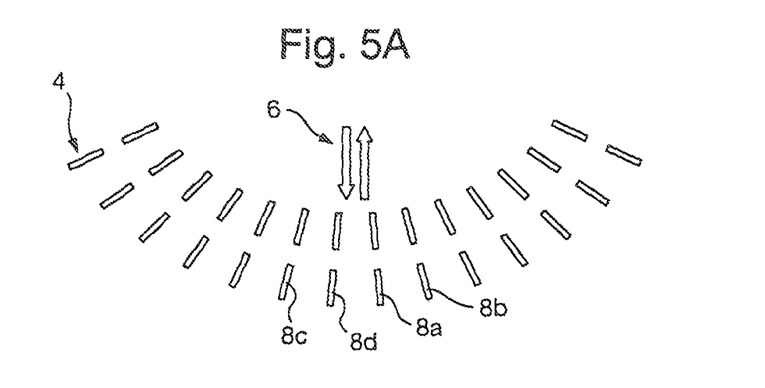
Figure 5B:
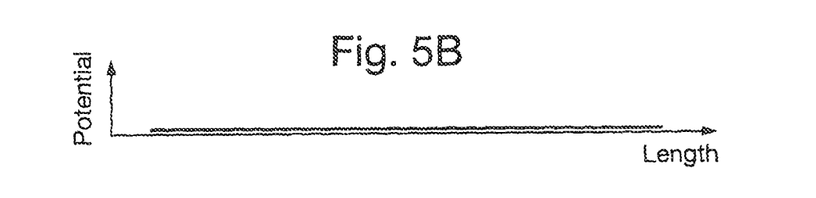
Figure 5C:
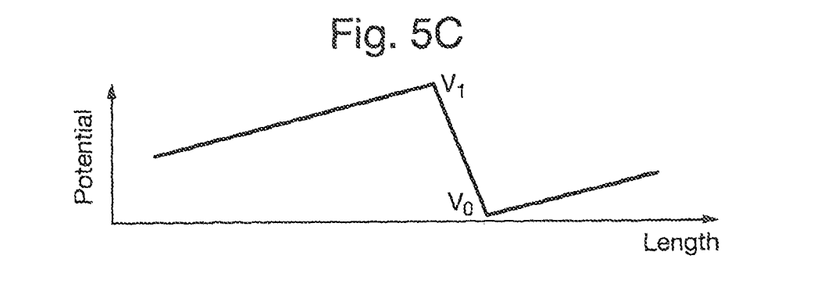
Figure 5D:
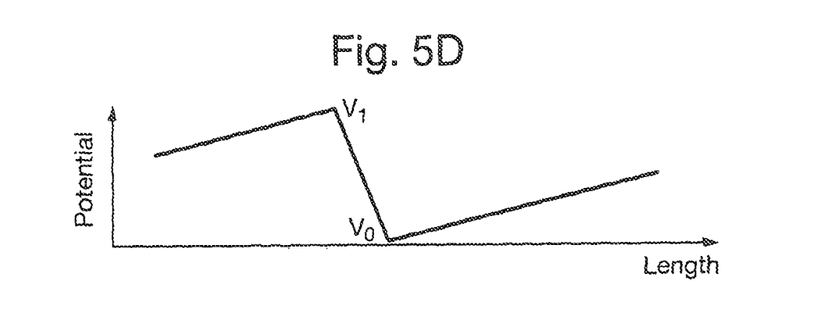

FIG. 5A shows the portion of the drift cell 4 of FIG. 4A at which ions may enter or exit the drift cell. FIGS. 5B to 5D show DC potential profiles along this portion of the drift cell 4 at different times during the ions separation process. In order to facilitate ion entry and ion exit at the same point on the circumference of the drift cell 4, ions are preferably arranged to enter or leave the drift cell in a region 6 of low DC potential. As shown in FIG. 5B, it is preferred that substantially no DC voltage gradient is arranged along the entrance/exit region 6 at the time that ions enter the drift cell 4. Once the ions are within the drift cell 4, an axial DC potential difference is then preferably applied. DC potentials are applied to the electrodes 8 around the drift cell 4 so as to form a voltage gradient as shown in FIG. 5C. A relatively high voltage $V_1$ may be applied at a first electrode 8a and progressively smaller DC voltages may be applied to the electrodes 8 around the drift cell 4 up to the last electrode 8b which is at $V_0$. As can be seen from FIG. 5C, the potential at the entrance region 6 is relatively high and the ions experience an axial electric field and begin travelling along the potential difference and around the device in a clockwise manner.

As described above, it is desired to apply a relatively high DC potential at the ion entrance region 6 in order to cause ions to begin to drift around the drift cell 4. It is also desired that the ions exit the device at a region 6 in which the DC potential is low or substantially zero. However, it is preferred for the ions to enter and exit the drift cell 4 at substantially the same location 6. According to the preferred embodiment both of these functions are enabled, with ions entering and exiting the device at the same location 6. The preferred embodiment achieves this by changing the DC potentials applied to the electrodes 8 with time such that the position of the voltage gradient moves around the drift cell 4. As described above, the potential profile shown in FIG. 5C causes ions to begin to drift around the drift cell 4 after they have entered the device. As the ions move around the drift cell the location of the potential difference also moves around the drift cell in a manner such that the ions experience the same uniform voltage gradient. By the time that the ions have passed around the drift cell to the exit region 6, the voltage gradient has rotated around the drift cell to the position shown in FIG. 5D. It can be seen that the low DC voltage $V_0$ has moved around the drift cell 4 to the position at electrode 8d and the high DC voltage $V_1$ has moved around the drift cell 4 to the position of electrode 8c. The portion of the axial DC potential difference that is arranged at the exit region 6 of the drift cell 4 therefore has a relatively low DC potential, enabling ions to exit the drift cell 4 in a region of substantially no or low DC potential.

As described above, if only a single cycle of the ions around the drift cell 4 is required, then the DC potentials preferably progress around the circumference such that the high voltage region at the entry/exit region 6 (substantially at $V_1$) is replaced by the low voltage region (substantially at $V_0$) by the time that the ions reach the exit region 6. In an alternative method, ions may enter the drift cell 4 and may then be transported to a confining region (not shown) that is located at some point away from the entry/exit region 6. The ions may be transported to the confining region using electric fields, such as by applying DC voltages to the electrodes 8. After the ions have been moved to the confining region a relatively high DC voltage $V_1$ may be applied at the confining region and a relatively low DC voltage $V_0$ may be applied at the entry/exit region 6, causing the ions to move around the drift cell 4. In this manner, it is not required to change the location of the axial DC voltage gradient that separates the ions in order to be able to extract ions at an exit region 6 having substantially no DC voltage. This approach of moving the ions away from the entry region prior to mobility separation can also be used in modes wherein ions are caused to cycle around the drift cell 4 multiple times.

Figure 6A:
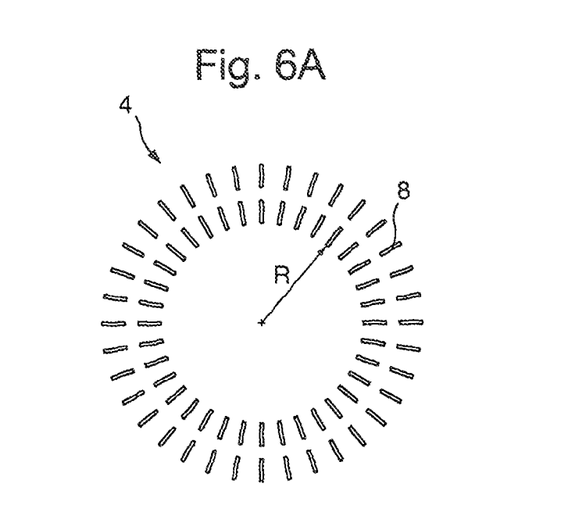
FIGS. 6A and 6B show an embodiment of a drift cell that is substantially the same as that shown in FIGS. 4A and 4B, except that the shape of the aperture in each electrode is different.
Figure 6B:
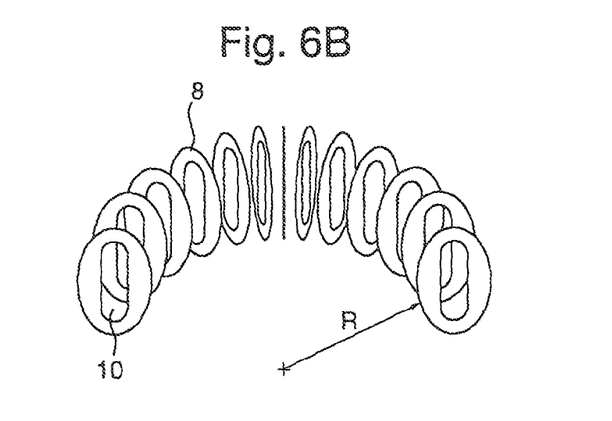

FIGS. 6A and 6B show an embodiment that is substantially the same as that shown in FIGS. 4A and 4B, except that the shape of the aperture 10 in each electrode 8 is different.

FIG. 6B shows a perspective view of some of the electrodes 8 making up the drift cell 4 of FIG. 6A. It will be seen that each electrode 8 has a slotted aperture 10 through which the ions pass as they travel around the drift cell 4. Each slot 10 preferably has its width arranged in the direction of the radius R of the cell drift 4 and its length perpendicular to the radius R of the drift cell 4. The use of slots 10 as opposed to other shaped apertures 10 allows a relatively high charge capacity of ions to be contained by the electrodes 8 whilst confining the ions at substantially the same radial distance R from the centre of the drift cell 4. This minimises the differences in electric field and path length that ions experience as they pass around the drift cell 4. It will be appreciated that if relatively large circular apertures 10 were used to confine a high charge density then ions at a relatively large radial distance R from the center of the drift cell 4 would experience a significantly different path length to ions at a relatively small distance R from the centre of the drift cell 4. It can be seen that the plane in which each electrode 8 is arranged is preferably aligned in a radial direction from the centre of the drift cell 4. The electrodes 8 therefore diverge from each other with increasing distance from the centre of the drift cell 4, causing the RF radial confinement to become less effective for ions at increasing radial distance R from the centre of the drift cell 4. The use of slotted apertures 10 enables a relatively high number of ions to be located at substantially the same radial position with respect to the centre of the drift cell 4, such that the ions experience substantially the same RF containment field.

In a closed loop device such as any of those described above, the range of mobilities that can be analysed in a given experiment is determined by the physical length of the drift field and the temporal length of the mobility experiment. For example, if the DC voltage gradient progresses around the drift cell 4 at a rate such that the lowest mobility ion species is retained at the point of the applied high potential $V_1$, then after a given time the highest mobility species will reach the end of the DC voltage gradient where the low potential $V_0$ is applied and no further ion mobility separation will occur for this species. If the ions of highest mobility have not reached the ion extraction point 6 by this time then there is a possibility that ions of lower mobility will re-merge with the ion of higher mobility, thus losing the ion mobility separation. This situation may be exacerbated if higher mobility resolution is required since more cycles of the ions around the drift cell 4 are required and so the temporal length of the mobility separation increases.

The present invention contemplates providing relatively high resolution ion mobility separation on a selected range of ion mobility species by synchronising the rate at which the DC voltage gradient is cycled around the drift cell 4 with the rate at which the ion mobility range of interest cycles around the drift cell 4. The synchronisation may be performed so as to allow ion species with undesirably low mobility to 'fall off' the DC voltage gradient at the high potential $V_1$ end and allow ions with undesirably high ion mobilities to leave the DC voltage gradient at the low potential $V_0$ end and re-merge with the other ions. The cycling rate of the DC voltage gradient can then be selected so that the low potential $V_0$ is arranged at the ion exit region 6 when the desired range of ion mobilities reaches this region for extraction. It is also contemplated that undesired ions that reach one or both ends of the DC voltage gradient may be eliminated or discarded from the system. This may be achieved, for example, by removing the RF ion confinement voltages applied to the electrodes 8 at points outside of the length along which the DC voltage gradient is maintained. The ions are then not radially confined at these points and will be lost to the system through diffusion.

Figure 7A:
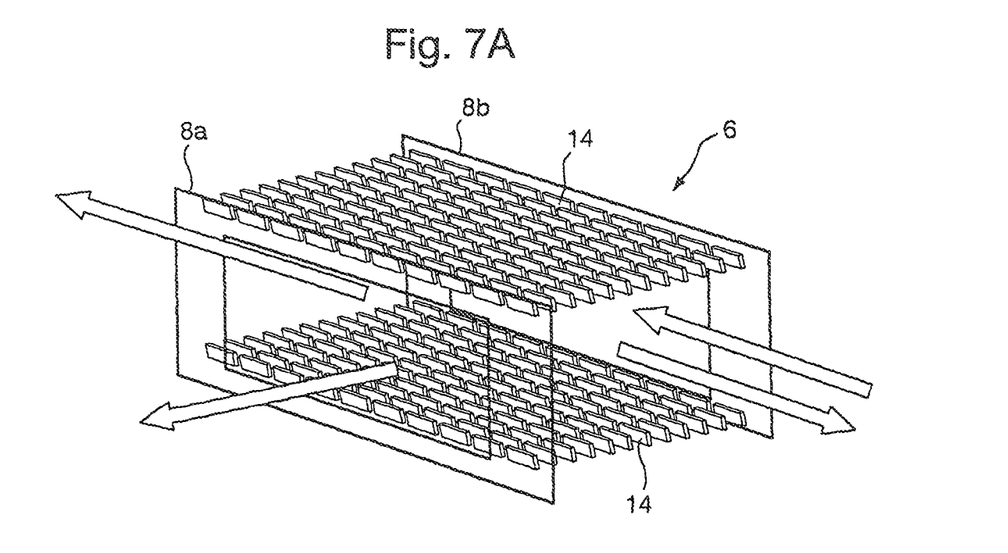
FIG. 7A shows a schematic of an ion entry/exit region of a drift cell of a preferred embodiment.
Figure 7B:
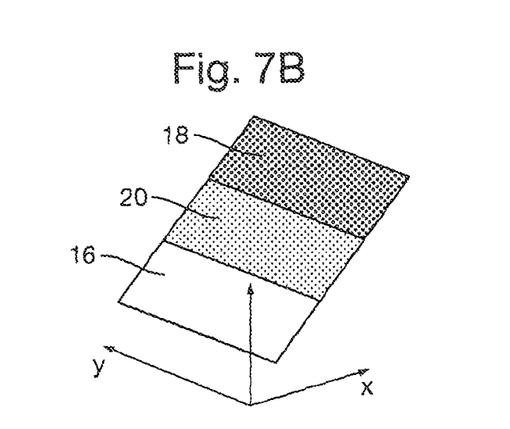
FIGS. 7B and 7C show the potentials of various parts of the entry/exit region at different times.
Figure 7C:
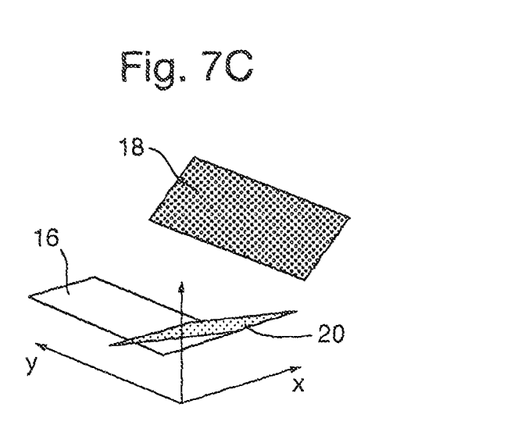

FIG. 7A shows a schematic of an ion entry/exit region 6 of the drift cell 4. FIGS. 7B and 7C show the potentials of various parts of the entry/exit region 6 at different times. Referring to FIG. 7A, the entry/exit region 6 comprises an array of entry/exit electrodes 14 arranged between two adjacent ones of the apertured electrodes 8a,8b. The entry/exit electrodes 14 preferably comprises a plurality of rows of upper electrodes and a plurality of rows of lower electrodes, wherein the rows are aligned with the planes in which the apertured electrodes 8a,8b are located. Each row of entry/exit electrodes 14 is preferably made up of a plurality of electrodes that may be axially separated along the length of each row. In order to radially confine the ions in the entry/exit region 6, RF potentials are preferably applied to the entry/exit electrodes 14. The same phase of the RF voltage supply is preferably applied to all of the entry/exit electrodes 14 that are in the same row. Different phases, preferably opposite phases, of the RF voltage supply are preferably applied to adjacent rows of the entry/exit electrodes 14 in order to radially confine the ions.

During on entry into the drift cell 4, voltages may be applied to the entry/exit electrodes 14 so as to generate a small electric field in the y-direction that encourages ions into the drift cell 4 through the side of the drift cell 4. Voltages may also be applied to the entry/exit electrodes 14 at the opposite side of the entry/exit region 6 to which the ions enter, so as to prevent the ions passing straight through and out of the drift cell 4. When it is desired to begin ion mobility separation, voltages applied to the entry/exit electrodes 14 are selected so as to apply an axial electric field in the x-direction that causes the ions to pass around the drift cell 4. FIG. 7B shows the potential profile formed by the entry/exit electrodes 14 and the apertured electrodes 8a,8b on either side thereof at this point in time. Potential profile 16 is the profile due to apertured electrode 8a, potential profile 18 is the profile due to apertured electrode 8b, and potential profile 20 is the profile due to entry/exit electrodes 14. When it is desired to cause ions to exit the entry/exit region 6, the potentials applied to the entry/exit electrodes 14 are preferably changed such that an electric field urges ions out of the device in y-direction. FIG. 7C shows the potential profile formed by the entry/exit electrodes 14 and the apertured electrodes 8a, 8b on either side thereof at this point in time. Potential profile 16 is the profile due to apertured electrode 8a, potential profile 18 is the profile due to apertured electrode 8b, and potential profile 20 is the profile due to entry/exit electrodes 14. Alternatively, it is contemplated that a voltage is successively applied to the entry/exit electrodes 14 in the y-direction towards the exit of the device so that a travelling potential wave propels ions out of the exit.

It will be appreciated that drift cells 4 having continuous ion guiding paths of shapes other than circular paths are also contemplated as being within the scope of the present invention. For example, a continuous oval or racetrack ion guide geometry may be employed.

Figure 8A:
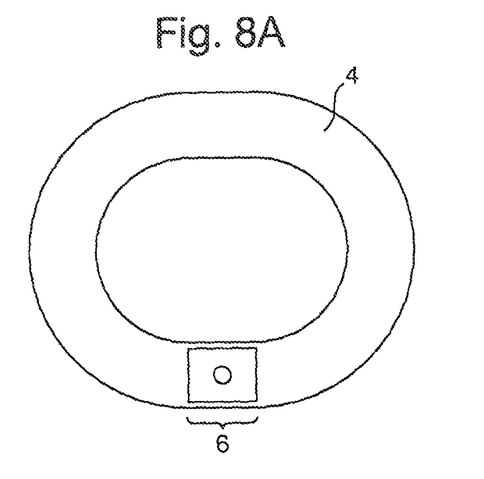
FIGS. 8A and 8B show different views of an ion mobility drift cell having an ion guide path that is of oval or racetrack geometry.

FIG. 8A shows a plan view of an ion mobility drift cell 4 having an ion guide path that is of oval or racetrack geometry. The drift cell 4 may be operated and constructed in substantially the same manner as any one of the embodiments described above, except that the electrodes 8 are arranged to form an ion guiding path that extends in a oval or racetrack shape, rather than a circular shape. The electrodes 8 of the drift cell 4 may be electrically connected to a printed circuit board. Ions enter and exit the drift cell 4 at ion entry/exit region 6. This entry/exit region 6 may be constructed in the same manner as in the above embodiments. Alternatively, the entry/exit region 6 may be configured so that ions can enter and exit the drift cell 4 in a direction that extends upwards above or downwards below the drift cell 4, rather than through the side of the drift cell 4 as in the above-described embodiments.

Figure 8B:
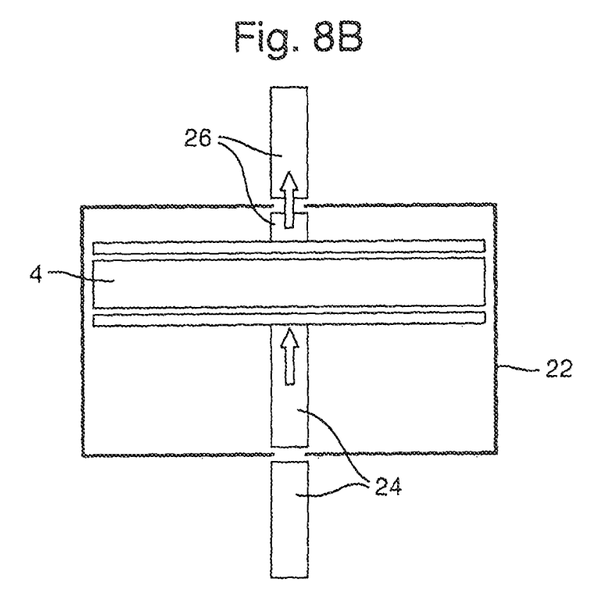

FIG. 8B shows the embodiment of FIG. 8A from a side view. The drift cell 4 is arranged inside a chamber 22 that is filled with drift gas. Ions are guided into and out of the chamber 22 using RF ion guides 24,26. The RF ion guides 24,26 are also coupled with the ion entry/exit region 6 of the drift cell 4 such that ions can be guided into the drift cell 4 and out of the drift cell 4. In this embodiment, ions are guided into the chamber 22 and into the entry/exit region 6 of the drift cell 4 from a direction below the drift cell 4 by input ion guides 24. If the ions are desired to be separated by their ion mobility then the ions are urged around the oval or racetrack ion path of the drift cell 4, in the same manner as in the above described embodiments. As the ions pass along the ion path they separate according to their ion mobility through the drift gas that is present in the chamber 22 and hence the drift cell 4. When ions are desired to be extracted from the drift cell 4 they are ejected in a direction upwards above the drift cell 4 and into the ion guides 26. The ions are then guided out of the chamber 22 by the ion guide 26. On the other hand, if ion mobility separation of the ions is not required then ion species can be caused to pass from the input ion guides 24 to the output ion guides 26 directly through the entry/exit region 6 of the drift cell 4 and without passing around the drift cell 4. In other words, the drift cell 4 may be operated in a by-pass mode.

In a preferred mode of operation, it is possible to extract ions having a desired range of ions mobilities from the drift cell 4. This is achieved by causing ions to traverse around the drift cell 4 so that they separate and then synchronising the activation of an ejection pulse at the ion entry/exit region 6 with the time at which the ions of interest are at the entry/exit region 6. The desired ions are therefore ejected from the drift cell 4 and the other ion species remaining in the drift cell 4 can continue to pass through the drift cell 4 and separate according to ion mobility. Alternatively, the remaining ions may be discarded from the drift cell 4, for example, by removal of the RF voltages from the electrodes 8 such that the ions are no longer radially confined within the drift cell.

The ejected ions having the desired ion mobilities can be immediately transported away from the drift cell 4 to a mass analyser or detector. Alternatively, such ions may be trapped in a storage region whilst the next mobility cycle occurs in the drift cell 4 and until more ions of the same ion mobility range are ejected from the drift cell 4 into the storage region. After sufficient mobility cycles have been performed to accumulate the desired number of ions in the storage region, these ions may then be transported to an analyser for further analysis or to a detector. This method may be used to increase the ion signal of the desired ions. Additionally, or alternatively, the desired ions that have been ejected from the drift cell 4 may be caused to fragment or dissociate and then reintroduced back into the drift cell 4 such that the ion mobilities of the fragment or daughter ions can be analysed by the drift cell 4.

It will be appreciated that in a mode of operation the ion guiding path of the drift cell 4 may be used to store ions and that the drift cell 4 may operate as an ion storage device.

Although the electrodes forming the drift cell have been described hereinabove as being apertured electrodes, it is also contemplated that other geometries of electrodes may be used to guide ions around the drift cell.

Figure 9A:
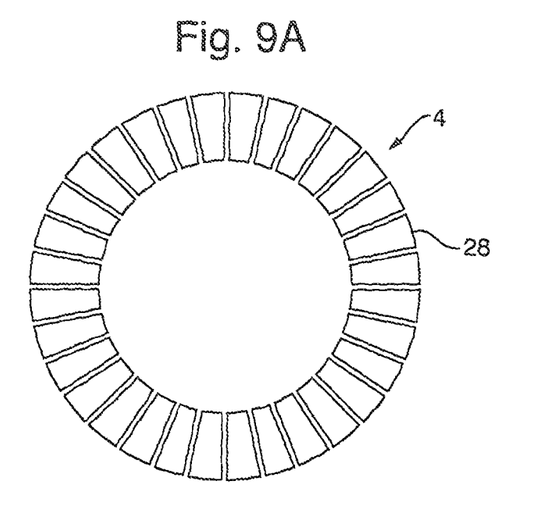
FIG. 9A shows a plan view of the arrangement of the electrodes in an embodiment of the present invention.

FIG. 9A shows a preferred embodiment of the arrangement of the electrodes in the drift cell 4 from a plan view. Rather than the drift cell 4 being formed from a plurality of apertured electrodes 8 that are arranged in a circle, the drift cell is divided into segments 28, wherein each segment 28 comprises a plurality of layers of electrodes, as shown in FIG. 9B.

Figure 9B:
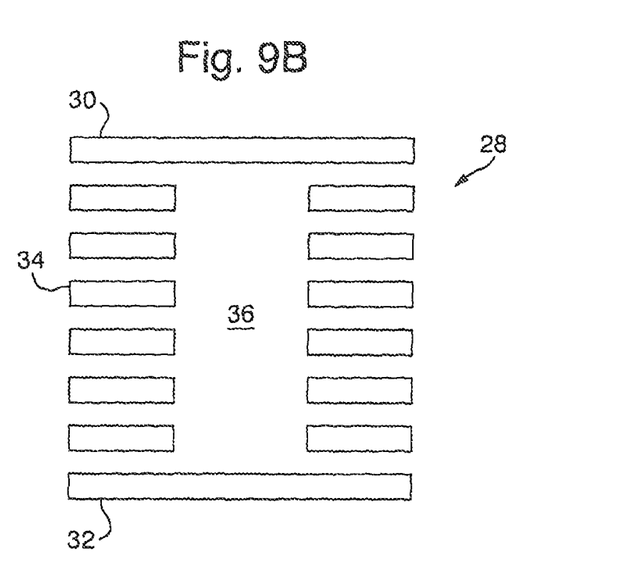
FIG. 9B shows a schematic of a cross section through the drift cell.

FIG. 9B shows a cross-section through one of the segments 28 in FIG. 9A. Each segment 28 is formed from a top electrode 30, a bottom electrode 32 and a plurality of layers of electrodes 34 arranged therebetween. Each layer comprises two laterally spaced apart electrodes 34 arranged such that these electrodes 34 form side electrodes. The side electrodes 35 are stacked in columns so as to define a space 36 between the columns of side electrodes 34, and between the top and bottom electrodes 30,32. The top, bottom and side electrodes 30,32,34 are substantially planar and extend around the longitudinal direction of the drift cell 4 so as to form a segment 28 of the drift cell 4 as shown in FIG. 9A. The planar electrodes 30,32,34 extend in the plane that ions travel in, in use.

Ions are radially confined within the space 36 between the side electrodes 34, top electrode 30 and bottom electrode 32. In order to achieve this confinement, RF potentials are applied to the side electrodes 34. The same phase of an RF voltage source is preferably applied to the two side electrodes 34 in each layer. Different phases of the RF voltage source are preferably applied to the side electrodes 34 in adjacent layers. The side electrodes 34 in any given layer are preferably supplied with an opposite RF voltage phase to the side electrodes 34 in the adjacent layers. By applying RF potentials to the side electrodes 34, the ions are laterally confined within the space 36 between the side electrodes 34. RF potentials may also be applied to the top and bottom electrodes 30,32 so as to confine ions within the space 36 in the vertical direction. However, it is preferred that only DC potentials are applied to the top and bottom electrodes 30,32 so as to confine the ions in the vertical direction.

Although the drift cell 4 has a different electrode configuration to the earlier described embodiments having apertured electrodes 8, the operation of the drift cell 4 is substantially the same. A DC voltage gradient is applied to at least some of the electrodes so as to provide an axial electric field that urges ions to drift through the drift gas and around the drift cell 4. The DC voltage gradient may be formed by supplying different DC voltages to the electrodes of different segments 28 of the drift cell 4. Different DC voltages may be supplied to the top 30 and/or bottom 32 electrode in different segments 28 so as to form the voltage gradient. Additionally, or alternatively, different DC voltages may be supplied to the side electrodes 34 of different segments 28 so as to form the voltage gradient. For example, progressively smaller DC voltages may be applied to the electrodes of the different segments 28 around the drift cell 4 so as to create a voltage gradient that drives the ions along the drift length.

As described in relation to the earlier embodiments, the DC potential difference applied to the device may be arranged along a fixed length of the device. Alternatively, the DC potential difference may be arranged along only a portion of the length of the drift region so as to form an axial electric field region and this axial electric field region may then be moved around the device with the ions. The exit region 6 may be configured as described previously.

Although the present invention has been described with reference to preferred embodiments, it will be understood by those skilled in the art that various changes in form and detail may be made without departing from the scope of the invention as set forth in the accompanying claims.

The invention claimed is:

1. A method of separating ions according to their ion mobility with an RF ion guide having a plurality of electrodes arranged to form an ion guiding path that extends in a closed loop, said method comprising:
supplying RF voltages to at least some of said electrodes in order to confine ions within said ion guiding path; and
maintaining a DC voltage gradient in a DC voltage gradient region along at least a portion of a longitudinal axis of said ion guide, wherein said voltage gradient urges the ions to undergo one or more cycles around said ion guide and thus causes the ions to separate according to their ion mobility as the ions pass along the ion guide;
wherein the DC voltage gradient moves around the ion guide at a rate such that at least some of said ions continually remain within the DC voltage gradient region as the ions travel around the ion guide and until such ions are extracted from the ion guide at an exit region of the ion guide.

2. The method of claim 1, wherein the ion guide comprises an ion entry/exit region configured for introducing ions into the ion guide in one mode and for extracting ions from the ion guide in another mode, wherein the ion entry/exit region is at a fixed location on the ion guide.

3. The method of claim 1, wherein the electrodes of the ion guide are axially spaced along the longitudinal axis of the ion guide and wherein different DC voltages are applied to different ones of said axially spaced electrodes so as to form said DC voltage gradient.

4. The method of claim 1, wherein the DC voltage gradient region is defined over a length of the ion guide extending from a first electrode at a relatively high potential to a second electrode at a relatively low potential.

5. The method of claim 4, wherein progressively smaller DC potentials are applied to electrodes between the first and second electrodes in a direction from the first electrode to the second electrode so as to form said voltage gradient.

6. The method of claim 1, wherein a substantially uniform DC voltage gradient is arranged along the DC voltage gradient region.

7. The method of claim 1, wherein the ions separate out according to their ion mobility within the DC voltage gradient region.

8. The method of claim 1, wherein the ions remain within the DC voltage gradient as the ions travel only a single cycle around the ion guide, or wherein the ions remain within the DC voltage gradient as the ions repeatedly travel multiple cycles around the closed loop ion guide.

9. The method of claim 1, wherein the DC voltage gradient moves around the ion guide at a rate such that undesired ions having an ion mobility above a first threshold value or below a second threshold value do not continuously remain within the voltage gradient region as the region is moved around the ion guide.

10. The method of claim 9, wherein undesired ions having an ion mobility above the first threshold value exit the low potential end of the voltage gradient region or undesired ions having an ion mobility below the second threshold value exit the high potential end of the voltage gradient.

11. The method of claim 9, wherein the undesired ions that do not continuously remain within the DC voltage gradient region are not extracted from the ion guide at an exit region of the ion guide.

12. The method of claim 1, wherein RF voltages are applied to the electrodes so as to confine ions within the ion guiding path along the DC voltage gradient region, and RF voltages are not applied to at least some of the electrodes at one or more regions of the ion guide outside of the DC voltage gradient region such that ions are not confined within said one or more regions of the ion guide and are lost from the ion guide at these regions.

13. The method of claim 1, wherein ions are introduced into the ion guide at an entrance region and wherein substantially a maximum potential of the voltage gradient is arranged at the entrance region at a time when the ions are in the entrance region so as to urge the ions away from the entrance region and around the ion guide.

14. The method of claim 1, wherein DC voltages are only applied to some of the electrodes of the ion guide such that the DC voltage gradient is arranged along only a portion of the length of the ion guide at any given time.

15. The method of claim 14, wherein at any given time the DC voltage gradient is arranged over a percentage of the length of the ion guide selected from: <5%; <10%; <20%; <30%; <40%; <50%; <60%; <70%; <80%; or <90%; or wherein at any given time the DC voltage gradient is arranged over a percentage of the length of the ion guide selected from: >5%; >10%; >20%; >30%; >40%; >50%; >60%; >70%; >80%; or >90%.

16. The method of claim 1, wherein the DC voltage gradient is arranged over substantially the whole length of the ion guiding region at any given time.

17. The method of claim 1, wherein the electrodes are configured to confine ions in directions perpendicular to the longitudinal axis of the ion guide when said RF voltages are applied.

18. The method of claim 1, wherein the electrodes are apertured electrodes that are aligned such that the ions are guided through the apertures of the electrodes as the ions travel along the ion guiding path.

19. The method of claim 18, wherein the apertures in the electrodes are slotted apertures.

20. The method of claim 19, wherein the electrodes are arranged such that at least a portion of the ion guiding path is curved and so has a radius of curvature, wherein each slot has its minimum dimension substantially parallel with said radius and its maximum dimension substantially perpendicular to said radius.

21. The method of claim 1, wherein the electrodes are arranged such that the closed loop ion guiding path is substantially circular or oval.

22. The method of claim 1, wherein a drift gas is arranged in said ion guide such that ions separate according to their mobility through the drift gas as the ions are urged along the ion guide.

23. The method of claim 1, wherein ions are introduced into or ejected out of the ion guide through a side of the ion guide.

24. The method of claim 1, wherein an array of electrodes is provided to urge ions into an entry region of the ion guide; or wherein an array of electrodes is provided in an exit region of the ion guide to urge ions out of the ion guide.

25. The method of claim 1, wherein ions are introduced into the closed loop ion guide through the top or bottom of the ion guide; or wherein ions are ejected out of the ion guide through the top or bottom of the ion guide.

26. A method of mass spectrometry comprising separating ions according to a method as claimed in claim 1.

27. A method of separating ions according to their ion mobility with an RF ion guide having a plurality of electrodes arranged to form an ion guiding path that extends in a closed loop, said method comprising:
- supplying RF voltages to at least some of said electrodes in order to confine ions within said ion guiding path; and
- maintaining a DC voltage gradient in a DC voltage gradient region along at least a portion of a longitudinal axis of said ion guide, wherein said voltage gradient urges the ions to undergo one or more cycles around said ion guide and thus causes the ions to separate according to their ion mobility as the ions pass along the ion guide;
- wherein as time progresses, the portion of the ion guide along which the DC voltage gradient is maintained is moved along the ion guide and a rate at which the DC voltage gradient moves around the ion guide is synchronized with a rate at which ions of interest are urged around the ion guide by the voltage gradient such that the ions of interest reach an exit region of the ion guide at a time when a minimum potential of the voltage gradient is arranged at the exit region of the ion guide.

28. A method of separating ions according to their ion mobility with an RF ion guide having a plurality of electrodes arranged to form an ion guiding path that extends in a closed loop, said method comprising:
- supplying RF voltages to at least some of said electrodes in order to confine ions within said ion guiding path; and
- maintaining a DC voltage gradient in a DC voltage gradient region along at least a portion of a longitudinal axis of said ion guide, wherein said voltage gradient urges the ions to undergo one or more cycles around said ion guide and thus causes the ions to separate according to their ion mobility as the ions pass along the ion guide;
- wherein the ion guide comprises an exit region and ions are ejected out of ion guide at the exit region as the ions travel around the ion guide by applying a voltage pulse to one or more electrodes of the ion guide, the timing of the voltage pulse being selected so as eject ions of a selected ion mobility as the ions pass through the exit region.

29. An ion mobility separator comprising:
- an RF ion guide having a plurality of electrodes arranged to form an ion guiding path that extends in a closed loop;
- an RF voltage supply for supplying RF voltages to said electrodes for confining ions within said ion guiding path; and
- a DC voltage supply arranged and adapted to maintain a DC voltage gradient in a DC gradient region along at least a portion of a longitudinal axis of said ion guide, wherein in use said voltage gradient urges ions to undergo one or more cycles around said ion guide and thus to cause the ions to separate according to their ion mobility as the ions pass along the ion guide;
- wherein the DC voltage supply is arranged and adapted so that in use the DC voltage gradient moves around the ion guide at a rate such that at least some of said ions continually remain within the DC voltage gradient region as the ions travel around the ion guide and until such ions are extracted from the ion guide at an exit region of the ion guide.

30. A mass spectrometer comprising an ion mobility separator as claimed in claim 29.

* * * * *